United States Patent [19]

Shaw

[11] Patent Number: 4,797,257

[45] Date of Patent: Jan. 10, 1989

[54] SLIDE HOLDER AND TIP LOCATOR

[75] Inventor: James D. Shaw, Hilton, N.Y.

[73] Assignee: Eastman Kodak Company, Rochester, N.Y.

[21] Appl. No.: 75,477

[22] Filed: Jul. 20, 1987

[51] Int. Cl.$^4$ .............................................. G01N 35/04
[52] U.S. Cl. ..................................... 422/65; 422/100; 73/864.91
[58] Field of Search ....................... 422/65, 64, 66, 63, 422/100; 73/864.91, 864.14

[56] References Cited

U.S. PATENT DOCUMENTS

| | | | |
|---|---|---|---|
| 4,231,989 | 11/1980 | Thoma | 422/100 |
| 4,287,155 | 9/1981 | Tersteeg et al. | 422/100 |
| 4,296,070 | 10/1981 | Montalto et al. | 422/65 |
| 4,332,768 | 6/1982 | Berglund | 422/100 |
| 4,539,855 | 9/1985 | Jacobs | 422/100 |
| 4,753,775 | 6/1988 | Ebersole et al. | 422/100 |

Primary Examiner—Benoit Castel
Assistant Examiner—Richard D. Jordan
Attorney, Agent, or Firm—Dana M. Schmidt

[57] ABSTRACT

There is disclosed a universal slide holder for use in an analyzer, that will accept either a colorimetric slide or a potentiometric slide for dispensing a liquid onto the slide. The holder comprises a body portion, means for releasibly holding a slide, and a disposable tip guide and support turret for positioning a tip relative to the slide during metering. The holder is improved in that the guide and support turret has two passageways extending through it to a position just above the slide holding means, with a construction to position a liquid dispensing tip selectively in one or the other passageway, the passageways including a shoulder dimensioned to position and support the dispensing tips based on the dimensions of the barrel of the tip.

4 Claims, 4 Drawing Sheets

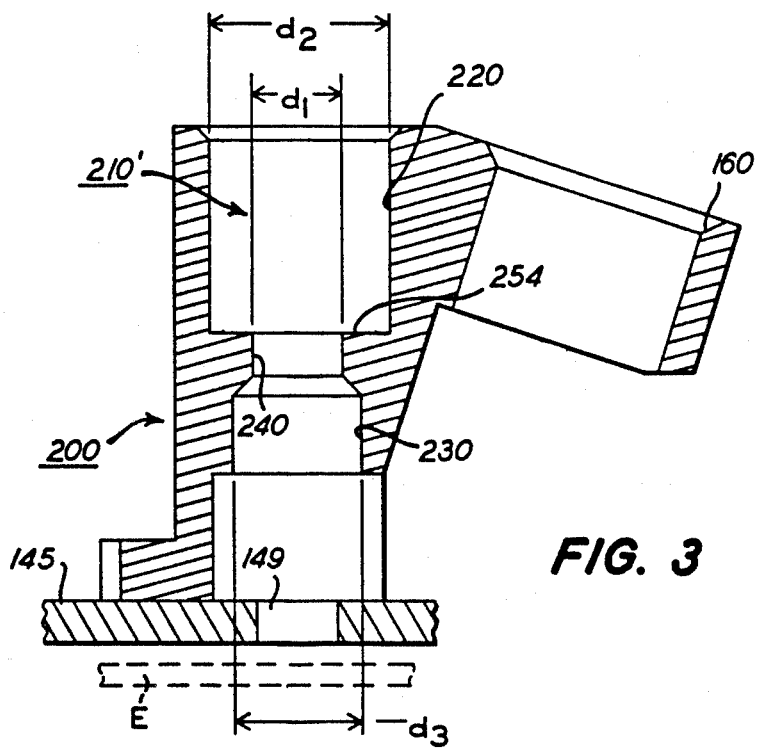
FIG. 3
FIG. 4
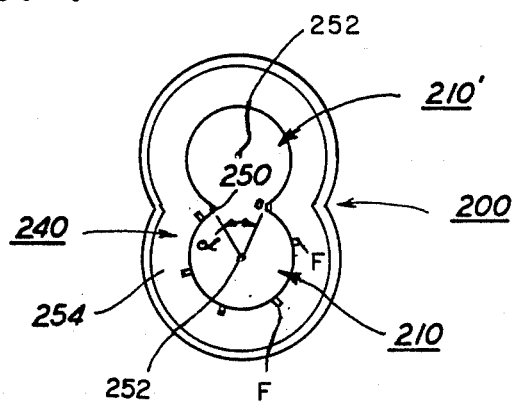

SLIDE HOLDER AND TIP LOCATOR

FIELD OF THE INVENTION

This invention relates to slide holders used in analyzers to ascertain analyte concentrations in liquid added to the slides.

BACKGROUND OF THE INVENTION

In the analyzer shown in U.S. Pat. No. 4,296,070, FIGS. 2-4 especially, two different slide blocks or holders 40 are provided to hold a test element or slide 15 or 17. One kind of slide 15 is a colorimetric test element, with a liquid-receiving area that is centered, FIG. 3. The other kind of slide 17 is a potentiometric test element with a sample liquid-receiving area that is offset from center. Also featured in the holder is a tip locator, unnumbered, shown as a vertically rising cylinder or turret, in FIG. 4. That tip locator is used to locate the dispensing tip from the metering tower 18, FIG. 2, relative to the slides, to permit liquid dispensing onto the slides. The holders 40 are rotated into position under the tower by rotation of rotor 32, FIG. 3, that mounts holders 40 at the ends of arms 36. As is evident in FIG. 3, the tip locator is slightly off-center for holders designed for slides 17, compared to the tip locator that is precisely centered for the holders designed for slides 15. Thus, each slide holder is dedicated to one type of slide or the other. Such dedication requires, among other things, a more complex software and timing program in order to keep track of which slide holder is appropriate for which kind of assay.

What has been needed prior to this invention is a universal slide or test element holder that will allow either type of slide to be held, and at the same time accommodate either the centered dispensing for slides 15, OR the offset dispensing for slides 17. The simplest procedure for doing that is of course to modify the tip locator so as to have two vertical passageways, each slightly offset relative to the other, so that a dispensing tip can be brought down to the center of a slide (if colorimetric), or to one side of center (if potentiometric). However, I discovered that a problem exists if this is done—the standard opening for the tips causes considerable overlap of the side-by-side passageways. This overlap gives incomplete positive location of the dispensing tip in the X-Y plane, and is unacceptable. Yet at the same time, such standard-sized opening has been needed to accommodate the dispensing tips used. It would be unacceptable to make such tips smaller overall to overcome that problem, for several reasons. Not the least of these reasons is that the molds used to mold the tips would have to be redesigned.

Therefore, there has been a substantial need to provide a universal slide holder for receiving in the analyzer either a colorimetric or a potentiometric slide, without requiring a redesign of the dispensing tip that cooperates with the slide holder during liquid dispensing.

SUMMARY OF THE INVENTION

I have discovered that the problem preventing the use of the overlapping passageways is that the present slide holders use bore diameters for the dispensing tips that are based on the outside diameter (O.D.) of the grasping fins. I have solved the problem by constructing the passageways so as to locate and hold the dispensing tips based on their barrel diameter, a smaller diameter than that of the grasping fins. The use of a smaller diameter means there is a reduction in the overlap of the passageways, leading to a satisfactory stability of the tips held by such improved slide holders.

More specifically, there is provided a slide holder for mounting a slide in an analyzer in position to receive liquid dispensed from a dispensing tip having a barrel and grasping fins, the holder comprising a body portion, means on the body portion for releasibly holding a slide constructed to assay for an analyte of a liquid, and a dispensing tip guide and support turret for positioning a dispensing tip in proper relationship to a held slide. The holder is improved in that the guide and support turret has two passageways extending therethough to a position just above the slide-holding means, located and constructed so that a liquid-dispensing tip is selectively positionable in one or the other passageway for dispensing liquid on either a colorimetric or potentiometric test slide, the passageways including a shoulder dimensioned to position and support such tips based on the barrel of the tip rather than the grasping fins, whereby any overlap of the passageways is minimized and the disposable tip is stabilized when positioned in one or the other passageway.

Accordingly, it is an advantageous feature of the invention that the same slide holder can be used to position the slide and the dispensing tip relative to each other, regardless of whether the slide is for colorimetric or for potentiometric assay, without necessitating a change in the construction or size of the dispensing tip.

It is a further advantageous feature of the invention that the positioning and centering of the dispensing tips within the passageways of the holder is independent of the width of the grasping fins, thereby making it possible to redesign the size of such fins without affecting the holder's function.

Other advantageous features will become apparent upon reference to the following Description of the Preferred Embodiments, when read in light of the attached drawings.

BRIEF DESCRIPTION OF THE DRAWINGS

FIG. 3 is a section view taken generally along the line III—III of FIG. 2;

FIG. 4 is a plan view of the tip locator turret only, enlarged for clarity;

DESCRIPTION OF THE PREFERRED EMBODIMENTS

Figure 1:
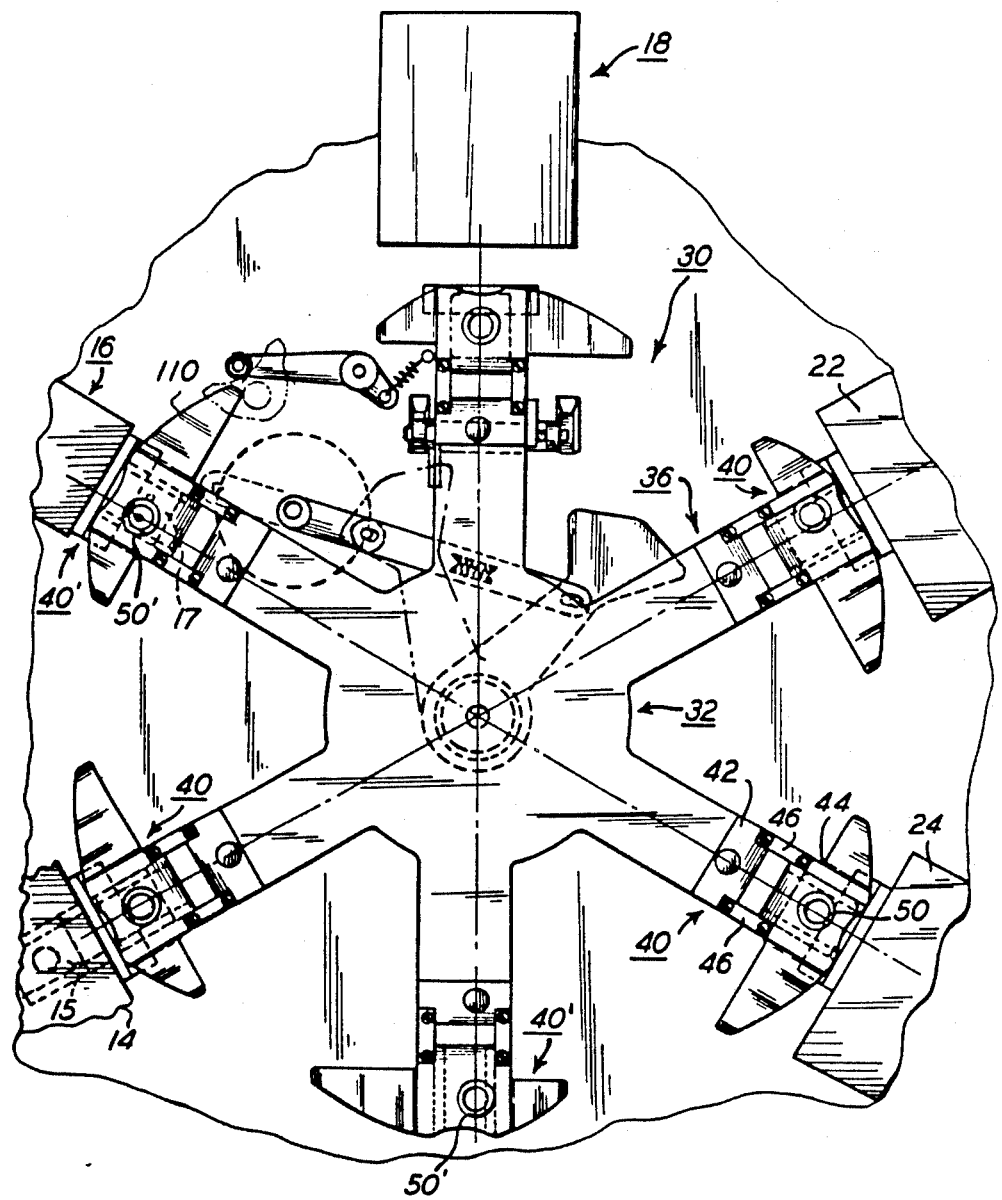
FIG. 1 is a fragmentary plan view of a portion of a prior art analyzer, in which the two different, dedicated slide holders are depicted.

The invention is described herein in connection with the preferred embodiments, that is, when used in conjunction with an analyzer for the analysis of liquids as described, for example, in U.S. Pat. No. 4,296,070. In addition, it is applicable to a slide holder for holding slides in any analyzer in which two different slides of any kind have to be accommodated, one of which receives dispensed liquid in the center, and the other of which receives such liquid off-center.

As used herein, terms such as "up", "down" and "vertical" refer to the orientation of parts as they are used in the analyzer.

The invention concerns slide holders of the type used in analyzers such as the analyzer shown in U.S. Pat. No. 4,296,070. Thus, in FIG. 1 herein, such an analyzer comprises two slide stations 14 and 16 for slides 15 and 17; a liquid-dispensing station 18; means 30 for moving slides from stations 14 and 16, to station 18 and to incubators 22 and 24; and means (not shown) for detecting signals generated by the slide in proportion to the analyte of the liquid that is present. The moving means 30 in turn comprises a rotor 32 with preferably six arms 36, each of which is mounted with a slide holder 40 or 40'. Such a holder comprises arm-attaching portion 42 screwed onto the arms 36, slide-holding portion 44, flexible arms 46 connecting portions 42 and 44, and tip locator turrets 50 and 50'. The only difference between each of holders 40 and 40' is the location of turrets 50 and 50', and the additional presence, not shown, of a guide on slide holder 40' allowing the deposition of reference fluid onto slides 17.

As noted in the Background of the Invention, such slide holders 40 and 40' are dedicated to receiving only one kind of slide, slides 15 and 17, respectively.

In accord with the invention, the slide holder 140 is improved so as to accept either slide 15, a colorimetric slide, or slide 17, a potentiometric slide. To that end, the tip locator turret is redesigned. Slide holder 140 comprises, FIG. 2, arm-attaching portion 142, slide-holding portion 144, flexible connector 147, the improved tip locator turret 200, and a reference proboscis locator sleeve 160. The arm-attaching portion 142, slide-holding portion 144, flexible connector 147 and reference proboscis locator sleeve 160 are conventional and need no further detailed discussion. Examples are described in, e.g., U.S. Pat. No. 4,296,070. The slide-holding portion 144 includes a flat plate 145, FIG. 3, on which turret 200 is mounted, and guides (not shown) are used to hold a slide E (shown in phantom), spaced from plate 145, as shown in greater detail in FIG. 5 of U.S. Pat. No. 4,296,070. Plate 145 is apertured at 149, in alignment with passageways 210 and 210' (FIG. 3). The referenced proboscis locator sleeve functions, as is conventional, to guide into and hold in place the dispensing portion of the analyzer that dispenses reference fluid onto a potentiometric slide, if in fact a potentiometric slide is present in the slide holder. It is not used if a colorimetric slide is present.

Figure 2:
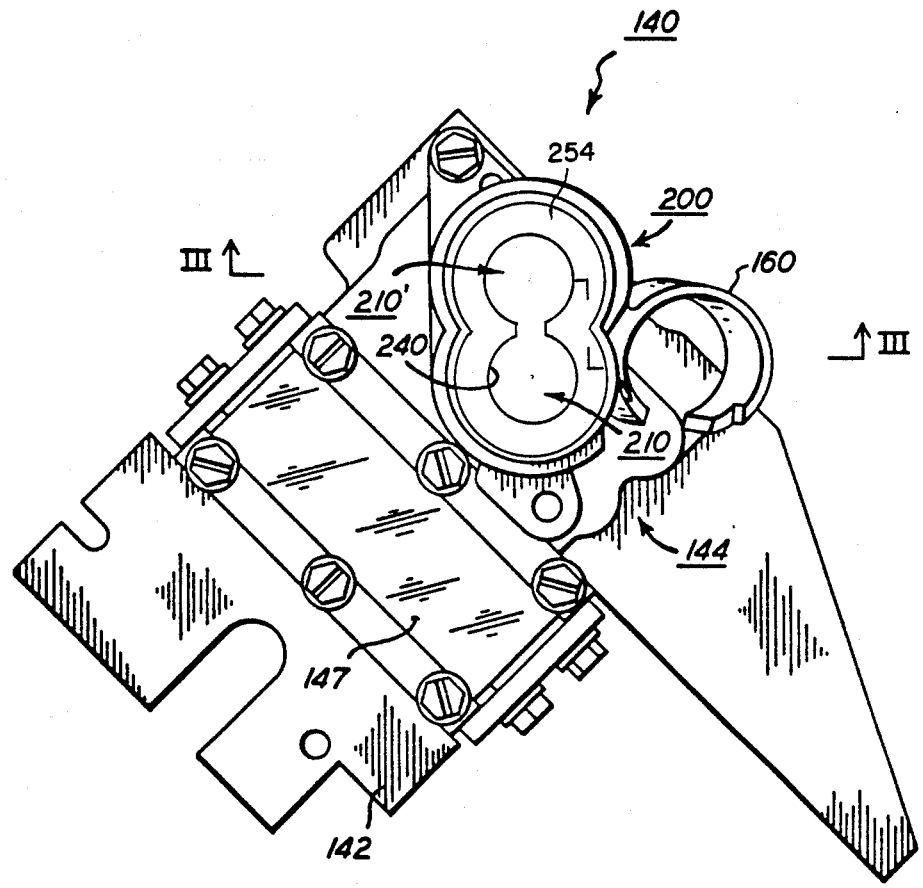
FIG. 2 is a plan view of a slide holder constructed in accordance with the invention.

Turning now to tip locator turret 200, this turret is similar to turrets 50 and 50' of FIG. 1 of the prior art except that two, rather than one, passageways 210 and 210', FIGS. 2-3, extend vertically through the turret. The passageways each have an upper portion 220 and a lower portion 230, with a tip-locating and supporting shoulder 240 located in between, FIG. 3.

Shoulder 240 is designed based on the barrel of the tip, rather than the grasping fins of the tip. As a result, FIG. 4, it is possible to have passageways 210 and 210' close enough together as required for dispensing onto both a potentiometric and a colorimetric slide, such that the overlap that occurs at their common sidewall forms a gap 250, that is of minimal size and therefore minimal interference in the support of dispensing tips. More specifically, gap 250 subtends an angle alpha, measured from either center 252 of passageway 210 or 210', that is no larger than about 60°. This leaves a supporting surface 254 for shoulder 240 that extends around for at least 315°.

The actual dimensions of passageways 210 and 210' depend of course, on the dimensions of the tip T that is used. For a tip T, FIG. 5, having an O.D. for the barrel B that is about 0.64 cm and a volume of about 240 $\mu$l, diameters $d_1$, $d_2$ and $d_3$, FIG. 3, are preferably the following approximate values:

$d_1 = 0.65$ cm
$d_2 = 1.27$ cm
$d_3 = 0.87$ cm

Each of the passageways 210 and 210' is preferably a substantial twin of the other, regarding dimensions.

Figure 5:
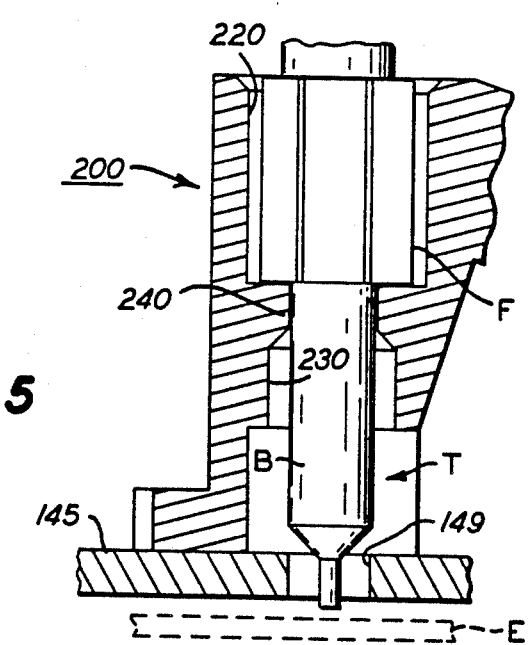
FIG. 5 is a fragmentary section view similar to that of FIG. 3, illustrating the use of the turret.
Figure 6:
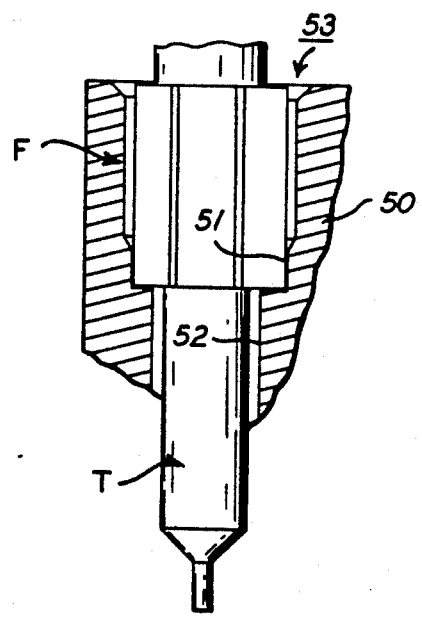
FIG. 6 is a fragmentary section view similar to that of FIG. 5, but of the prior art for comparison purposes.

The operation of the slide holder of this invention will be apparent from the preceding description. Thus, a dispensing tip T, FIG. 5, is held in turret 200, by reason of shoulder 240 having a bore size fitted to the barrel B of tip T, rather than to the grasping fins F, as has been conventional. As is apparent from FIG. 4, the included angle between fins on the tip is 60°, so that when angle alpha is less than 60°, at its maximum, then the fins F, shown as rectangular spikes resting on surface 254, can have only one at most fall into the gap 250. Gaps larger than this, for example a gap of 78° as is formed if shoulder 240 is dimensioned to hold the fins F, as in the prior art, FIG. 6, rather than the barrel B of the tip, lead to at least two of the fins being unsupported. That is, turret 50 had shoulders 51 sized to fit the O.D. of fins F of tip T. The lower portion 52 of passageway 53 had no relationship to the barrel dimension, except that it was substantially larger. As a result, tip T was not properly supported in a vertical orientation when both passageways were present.

Most preferably, angle alpha of FIG. 4 is about 40°.

As will be readily apparent from the above description, the slide holder of the invention will allow the grasping fins F to be modified in size, without necessitating a redesign of the passageways. That is, upper portion 220 will accommodate the present-sized fins that are preferably about 1.1 cm in diameter, or ones that are of lesser diameter. Such lesser diameter is advantageous to allow the dispensing tips T to fit into serum containers that are smaller in diameter, for example, those that are 10.2 mm in internal diameter.

The invention has been described in detail with particular reference to preferred embodiments thereof, but it will be understood that variations and modifications can be effected within the spirit and scope of the invention.

What is claimed is:

1. In a slide holder for mounting a slide in an analyzer in position to receive liquid dispensed from a dispensing tip having a barrel and grasping fins, the holder comprising a body portion, means on said body portion for releasably holding a slide constructed to assay for an analyte of a liquid, and a dispensing tip guide and support turret for positioning a dispensing tip in proper relationship to a held slide;

the improvement wherein said guide and support turret has two passageways extending therethough to a position just above said slide-holding means, constructed so that a liquid-dispensing tip is selectively positionable in one or the other passageway for dispensing liquid on either a colorimetric or potentiometric slide, said passageways including a shoulder dimensioned to position and support such tips based on the barrel of the tip rather than the grasping fins, whereby any overlap of said passageways is minimized and the disposable tip is stabilized when positioned in one or the other passageway.

2. A slide holder as defined in claim 1, wherein said shoulders of said passageways overlap at a common surface thereof, said overlap, as measured by the angle subtended from the center of either passageway, is less than about 60°.

3. A slide holder as defined in claim 1, wherein said passageways have an upper portion and a lower portion with said shoulder inbetween, the internal diameter of the upper portion being larger than that of said lower portion to accommodate the grasping fins of the disposable tip.

4. A slide holder as defined in claim 3, wherein the internal diameter of each of said passageways, measured at said shoulder, does not exceed about 0.68 cm for a disposable tip constructed to accommodate 240 $\mu$l of liquid.

* * * * *